United States Patent
Miao et al.

(10) Patent No.: US 9,678,002 B2
(45) Date of Patent: Jun. 13, 2017

(54) METHOD AND SYSTEM FOR NIR SPECTROSCOPY OF MIXTURES TO EVALUATE COMPOSITION OF COMPONENTS OF THE MIXTURES

(71) Applicants: Toni Zhang Miao, Orinda, CA (US); Ajit Ramachandra Pradhan, Walnut Creek, CA (US); Michael Edward Moir, San Rafael, CA (US); Eddy Lee, Hercules, CA (US); Ian Phillip Benson, The Woodlands, TX (US)

(72) Inventors: Toni Zhang Miao, Orinda, CA (US); Ajit Ramachandra Pradhan, Walnut Creek, CA (US); Michael Edward Moir, San Rafael, CA (US); Eddy Lee, Hercules, CA (US); Ian Phillip Benson, The Woodlands, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 14/526,903

(22) Filed: Oct. 29, 2014

(65) Prior Publication Data

US 2016/0123872 A1  May 5, 2016

(51) Int. Cl.
  *G01J 5/02* (2006.01)
  *G01N 21/3577* (2014.01)
  *G01N 21/359* (2014.01)

(52) U.S. Cl.
  CPC ....... *G01N 21/3577* (2013.01); *G01N 21/359* (2013.01); *G01N 2201/12746* (2013.01)

(58) Field of Classification Search
  CPC .......... G01N 21/359; G01N 2201/129; G01N 21/3563; G01N 21/3577;
  (Continued)

(56) References Cited

U.S. PATENT DOCUMENTS 4,940,900 A * 7/1990 Lambert ............... G01N 21/359
                                                      250/227.11
5,360,972 A * 11/1994 DiFoggio ............. G01N 21/359
                                                      250/339.09

(Continued)

*Primary Examiner* — David J Makiya
*Assistant Examiner* — Taeho Jo
(74) *Attorney, Agent, or Firm* — E. Joseph Gess; Melissa M. Hayworth; Susan M. Abernathy

(57) ABSTRACT

A method of estimating the relative concentration of at least two components contained in a mixture of the components is disclosed. At least two mixtures are produced by combining the at least two components, each of the at least two mixtures having different concentrations of the at least two components. NIR mixture spectra are acquired from each of the at least two mixtures. The NIR component spectra and the NIR mixture spectra are input into a computer utilizing chemometrics software and the spectra are analyzed to produce a calibration model for each component and each of the mixture NIR spectra. NIR monitored spectra for a monitored mixture of the components having an unknown concentration of the components is acquired. The calibration models are applied to the NIR monitored spectra to thereby estimate the concentration of at least one of the components in the monitored mixture.

14 Claims, 9 Drawing Sheets

(58) Field of Classification Search
CPC .......... G01N 2201/12753; G01N 2201/12746; G01N 2021/3595
USPC .................................................. 250/339.09
See application file for complete search history.

(56) References Cited

U.S. PATENT DOCUMENTS

| | | | | |
|---|---|---|---|---|
| 5,446,681 | A * | 8/1995 | Gethner | G01N 21/359 702/27 |
| 5,532,487 | A * | 7/1996 | Brearley | B01J 19/0006 250/339.07 |
| 5,699,269 | A * | 12/1997 | Ashe | G01N 33/2823 436/29 |
| 6,087,662 | A * | 7/2000 | Wilt | G01N 33/2823 250/339.09 |
| 6,159,255 | A * | 12/2000 | Perkins | C10L 1/06 250/339.07 |
| 6,507,401 | B1 * | 1/2003 | Turner | E21B 47/102 356/417 |
| 6,639,044 | B2 * | 10/2003 | Dessipri | C08G 8/10 250/339.09 |
| 6,662,116 | B2 * | 12/2003 | Brown | G01N 21/35 436/29 |
| 6,754,543 | B1 * | 6/2004 | Wold | G01N 21/359 700/29 |
| 6,897,071 | B2 * | 5/2005 | Sonbul | G01N 21/359 28/164 |
| 7,067,811 | B2 * | 6/2006 | Long | G01N 21/359 250/339.09 |
| 8,759,775 | B2 * | 6/2014 | Forrester | G01N 33/2829 250/339.12 |
| 2001/0037182 | A1 * | 11/2001 | Hall | G01J 3/28 702/104 |
| 2002/0084415 | A1 * | 7/2002 | Kawano | G01N 21/03 250/339.09 |
| 2004/0033617 | A1 * | 2/2004 | Sonbul | G01N 21/359 436/171 |
| 2004/0069942 | A1 * | 4/2004 | Fujisawa | E21B 47/102 250/269.1 |
| 2004/0084623 | A1 * | 5/2004 | Long | G01N 21/359 250/339.12 |
| 2006/0190137 | A1 * | 8/2006 | Free | G05B 17/02 700/266 |
| 2008/0233656 | A1 * | 9/2008 | Karl | G01N 21/78 436/93 |
| 2009/0105966 | A1 * | 4/2009 | Brown | G01N 33/2823 702/30 |
| 2011/0083842 | A1 * | 4/2011 | Indo | E21B 49/10 166/250.01 |
| 2012/0158315 | A1 * | 6/2012 | Trygstad | G01N 21/3577 702/25 |
| 2012/0160015 | A1 * | 6/2012 | Ovalles | G01N 30/88 73/61.52 |
| 2012/0226653 | A1 * | 9/2012 | McLaughlin | G01N 21/359 706/52 |
| 2013/0056201 | A1 * | 3/2013 | Chandler, Jr. | E21B 49/02 166/254.2 |
| 2013/0080070 | A1 * | 3/2013 | Pai | G06F 19/707 702/19 |
| 2013/0125630 | A1 * | 5/2013 | Collins | E21B 43/20 73/64.56 |
| 2013/0261224 | A1 * | 10/2013 | Deshpande | C08F 10/02 523/303 |
| 2013/0271758 | A1 * | 10/2013 | Marchant | B82Y 15/00 356/301 |
| 2014/0088876 | A1 * | 3/2014 | Shiley | G01V 13/00 702/8 |
| 2014/0273150 | A1 * | 9/2014 | Angel | C02F 3/342 435/186 |
| 2014/0349406 | A1 * | 11/2014 | Higgins | G01N 33/1833 436/60 |
| 2015/0106031 | A1 * | 4/2015 | Koseoglu | G01N 21/3577 702/24 |
| 2015/0136962 | A1 * | 5/2015 | Pomerantz | E21B 47/00 250/255 |
| 2015/0160179 | A1 * | 6/2015 | Atkinson | G01N 31/22 436/60 |
| 2016/0097757 | A1 * | 4/2016 | Sieben | G01N 1/28 436/60 |

* cited by examiner

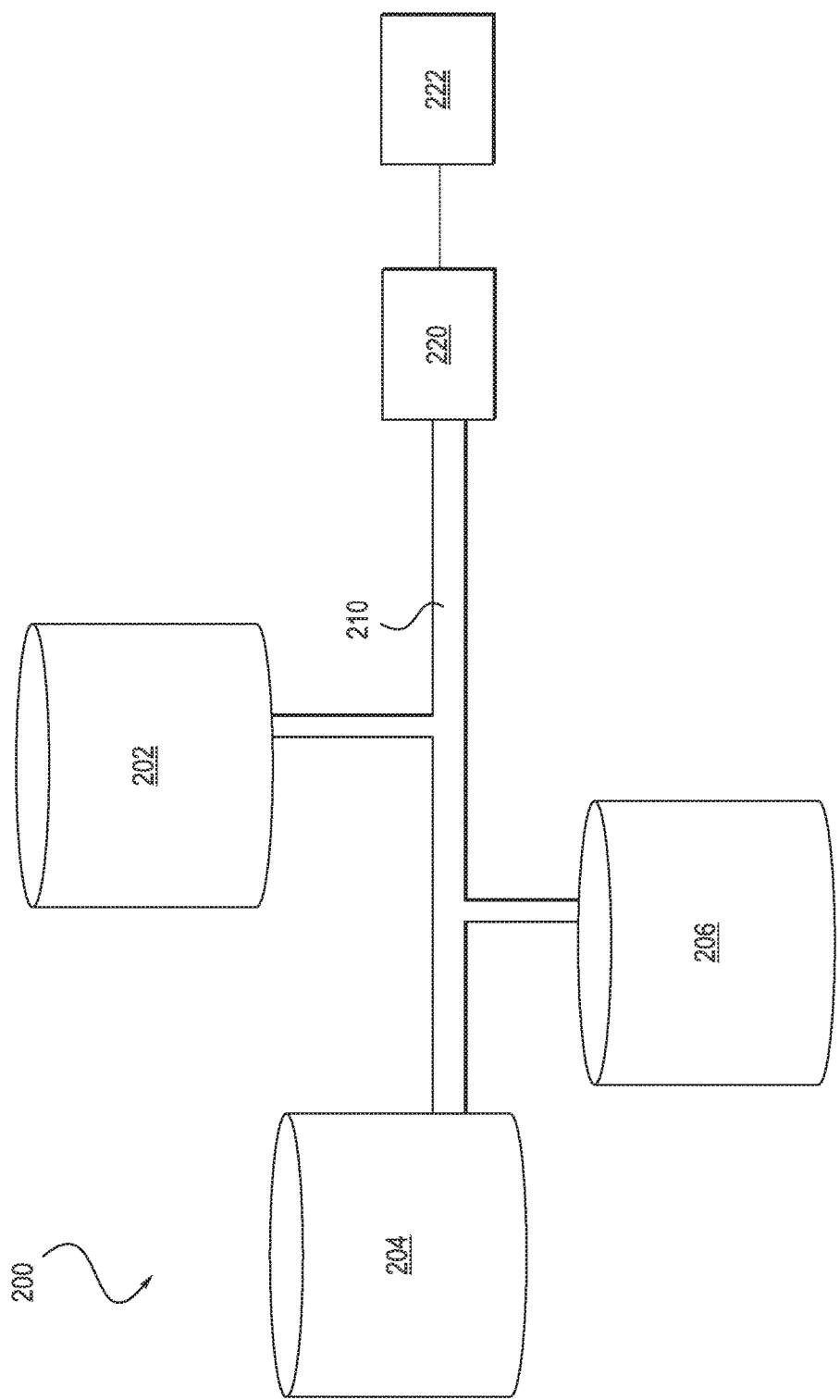

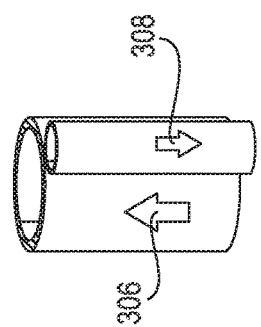
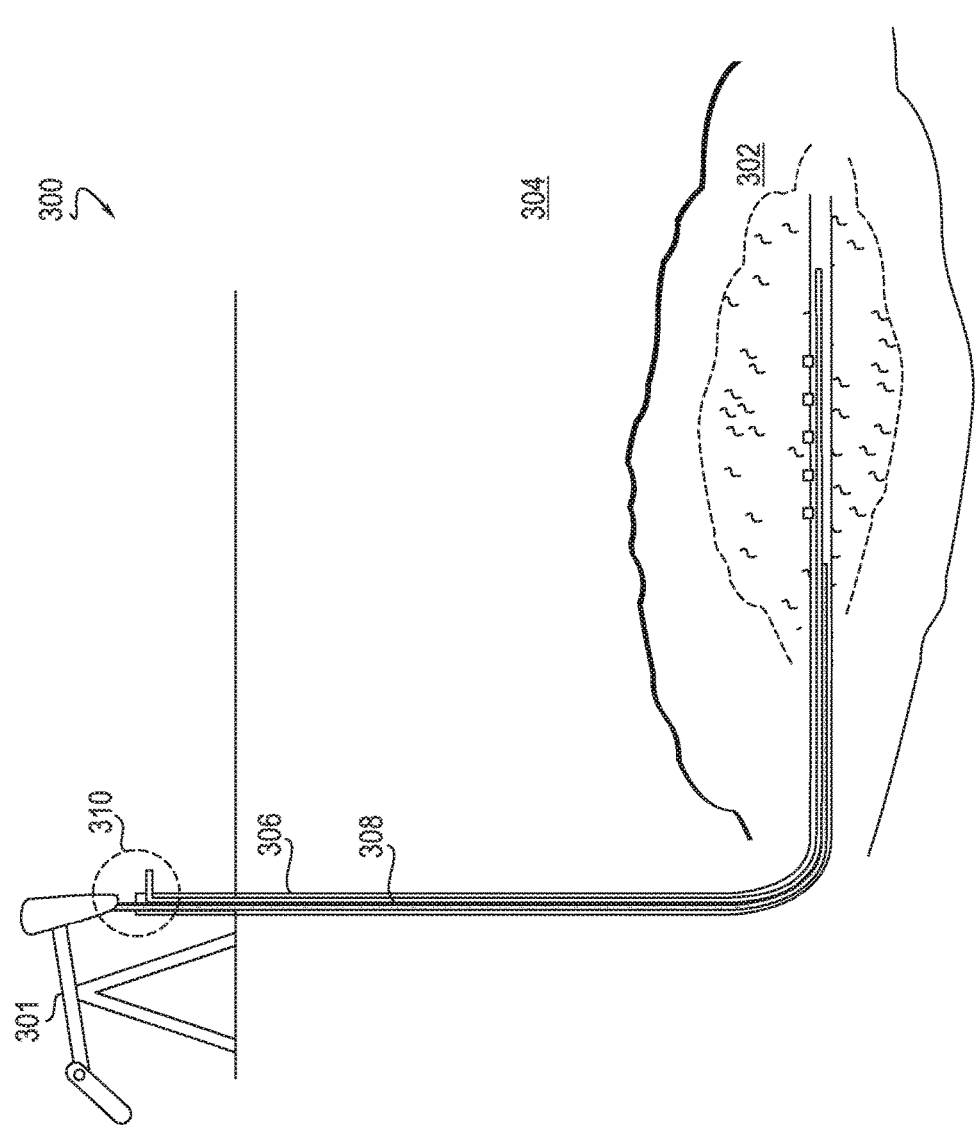

METHOD AND SYSTEM FOR NIR SPECTROSCOPY OF MIXTURES TO EVALUATE COMPOSITION OF COMPONENTS OF THE MIXTURES

TECHNICAL FIELD

This invention relates to the use of NIR spectroscopy for the analysis of chemical compositions, and more particularly, for the near real time analysis of components during production of hydrocarbons.

BACKGROUND

Solvent-based heavy oil recovery techniques can greatly enhance the recovery of heavy oil, extra-heavy oil and bitumen from subterranean reservoirs for both cold and hot applications. Cyclic and continuous injection of solvents reduces oil viscosity which increases oil production rates. Co-injection of solvent in a continuous or cyclic thermal EOR operation increases oil production rates, reduces steam requirements and may increase oil recovery. Solvent recovery is measured in the produced fluid stream to monitor processes and measure the amount of solvent that is recovered from the reservoir. Current methods for measuring the amount of solvent in such produced fluids are slow and sometime inaccurate. For example, the density of produced or monitored production fluids can be used to obtain rough estimates of the concentration of solvents in the production fluids.

Near-infrared spectroscopy (NIR) provides information on chemical and physical properties of sample components. Chemometric methods based on eigenvalue decomposition of a data matrix are effective tools for analyzing correlations between spectral information and compositions and properties. Principal component analysis (PCA) and partial least squares in latent variables (PLS) are commonly used techniques. NIR spectroscopy, in combination with chemometrics, is hence a powerful approach for fast routine and on-line chemical analyses.

A shortcoming of previous attempts to use NIR for analysis is that a plurality of components in a mixture of such components cannot be simultaneously analyzed as previous methods generally provide only analysis of one component at a time. Hydrocarbons and other liquids from several sources are often commingled. There is a need to determine the amount or content of these liquid mixtures of commingled fluids from several sources. This need is addressed by the present disclosure.

SUMMARY OF INVENTION

A method is disclosed of estimating the relative concentration of components contained in a mixture of the components. At least two components are acquired which are to be analyzed in a mixture containing the components. NIR spectra are acquired for each of the components to be analyzed. At least two mixtures are produced by combining the at least two components, each of the at least two mixtures having different concentrations of the at least two components. NIR mixture spectra are acquired from each of the at least two mixtures. The NIR component spectra and the NIR mixture spectra are input into a computer utilizing chemometrics software and the spectra are analyzed to produce a calibration model for each component and each of the mixture NIR spectra. NIR monitored spectra for a monitored mixture of the components having an unknown concentration of the components is acquired. The calibration models are applied to the NIR monitored spectra to thereby estimate the concentration of at least one of the components in the monitored mixture.

The sources of the components may be received from individual storage tanks of components. The storage tanks may contain hydrocarbons of differing compositions. Alternatively, the components may be received from different pipelines to produce the mixture of components to be analyzed as the monitored mixture. Alternatively, the sources of the components may be a plurality of subterranean reservoirs containing hydrocarbons of differing compositions.

In an alternative embodiment, the components are received from a wellbore in fluid communication with a subterranean formation containing heavy oil. The components may include water, solvent and heavy oil. At least the concentration of the solvent will be monitored as one of the components. Solvent may be added to the subterranean formation if the concentration of solvent in the monitored mixture falls below a predetermined concentration. This addition may be done continuously or in a batch manner. The monitored mixture from the wellbore is measured downstream from the wellbore. Produced fluids from the wellbore may be separated into gas, water, solvent and heavy oil with the monitored mixture being the separated solvent and heavy oil.

NIR technology is used to determine the composition of heavy crude oil mixtures with high accuracy. The mixtures studied in one embodiment include a naphtha diluent mixed with two heavy oil components.

Chemometric statistical processing can be used including Partial Least Squares (PLS) regression to model the spectral response of CH, $CH_2$ and $CH_3$ to various fluid types. This methodology is shown to be applicable for solvent-based EOR processes, reservoir management and reservoir characterization.

BRIEF DESCRIPTION OF THE DRAWINGS

These and other objects, features and advantages of the present invention will become better understood with regard to the following description, pending claims and accompanying drawings where:

FIG. 5 is a schematic of a mixture of commingled hydrocarbons received from discrete tanks which are then evaluated by NIR to determine the relative amounts received from each tank;

FIG. 6A is a schematic drawing of a production system wherein heavy oil, gas, water and naphtha solvent are produced from a subterranean reservoir via a wellbore with naphtha then being separated and reinjected into the reservoir;

FIG. 6B is an enlarged fragmentary view from FIG. 6A showing a reinjection line in production tubing used to reintroduce recovered naphtha or supplemental naphtha back in the reservoir.

DETAILED DESCRIPTION OF THE DISCLOSURE

In one embodiment, the relative concentration of components contained in a mixture of the components is accurately estimated. Calibration standards of solvent in crude oils mixture are accurately prepared described as follows. At least two components are first received from discrete sources. At least two calibration mixtures are then produced by combining the at least two components so that the at least two calibration mixtures have different concentrations of the components. In one embodiment, each of the components is from 5 weight % to 85 weight % of each of the calibration mixtures. In one embodiment, the calibration mixture includes at least one hydrocarbon that is liquid in the NIR device and at least one liquid solvent. In one embodiment, the calibration mixture includes two liquid hydrocarbons and at least one liquid solvent.

Suitable solvents for use in the mixture can include, but are not limited to, naphtha, volatile alkane solvents including propane, butane, octane, refined hydrocarbon solvents and solvent mixtures. Suitable solvents are in the liquid phase in the NIR device.

A near infrared (NIR) spectrum is acquired for each of the calibration mixtures using an NIR spectrometer.

The respective concentrations and calibration spectra acquired by the NIR spectrometer for each of the calibration mixtures are then input into a chemometrics software program on a computer and a mixture calibration is generated. Partial Least Squares (PLS) regression is applied to model the spectral response of $CH$, $CH_2$ and $CH_3$ to the chemical properties. The first overtone bands from 6.500 to 4,700 $cm^{-1}$ and the combination bands from 4,700 to 4000 $cm^{-1}$ can be used for the modeling. In one embodiment, these calibration models are retained in the memory of the computer to estimate further unknown components.

A monitored spectrum for a monitored mixture of the components is then acquired by NIR, and input into the chemometrics software.

Finally, the concentration of the components of the monitored mixture is calculated utilizing the mixture calibration.

Components and Component Spectra

Figure 1:
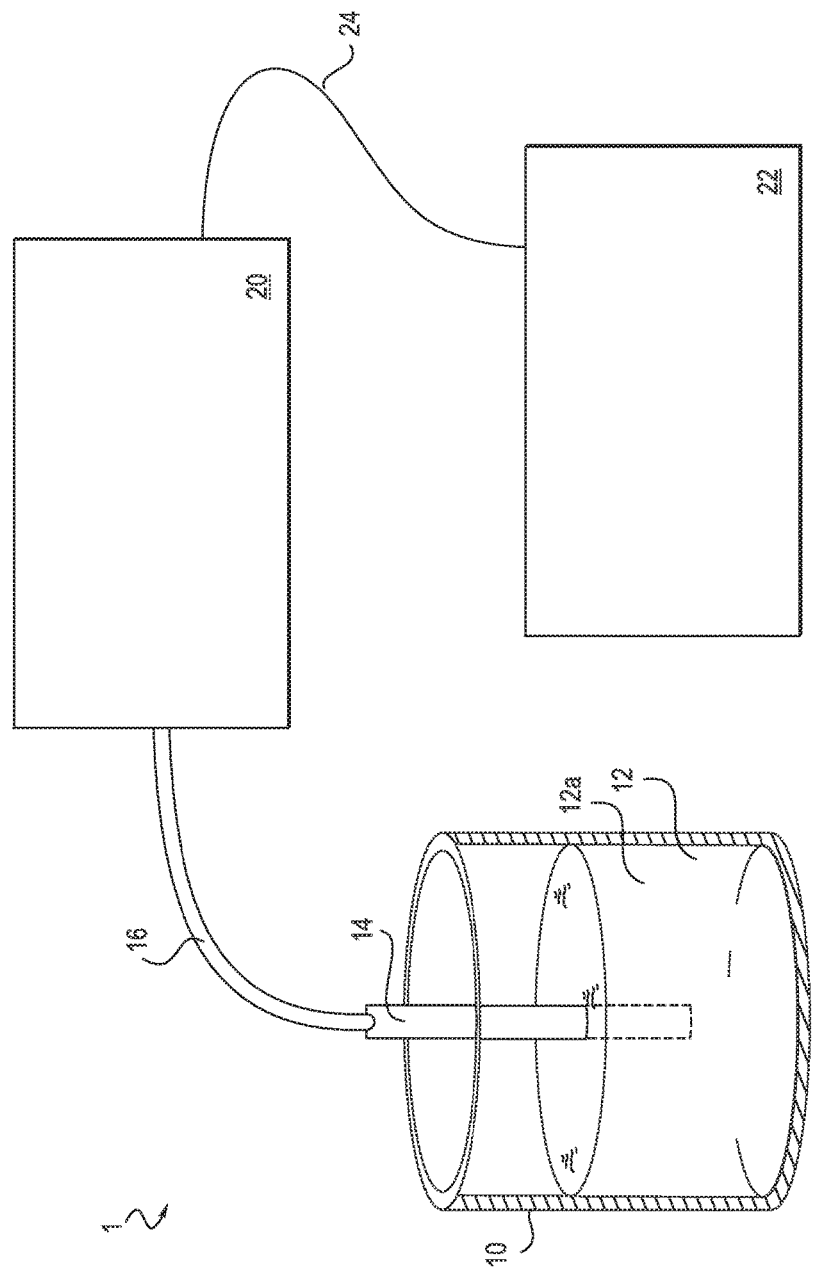
FIG. 1 is a schematic drawing of a probe connected to a spectrometer and computer, the spectrometer generating an NIR spectrum associated with a mixture of components to be analyzed and the spectrum being input to the computer.

FIG. 1 is schematic drawing of a test system 1 showing a beaker 10 containing a liquid component 12(a) which is to be subject to analysis for its presence when commingled with one or more other components forming a mixture 12. In this particular example, the component 12(a) is a heavy crude oil sample. Components in mixture 12 might include crude oil samples such as heavy oil (API<12), light oil (API>40), solvents such as naphtha, water, etc. For the purposes of this specification, naphtha is defined as hydrocarbons boiling in the range from 30° C. to 200° C. By way of example and not limitation, other components which may be analyzed in a mixture of components may include polymeric components and diesel components.

While Mid-IR spectroscopy makes use of fundamental vibrations, Near-IR spectroscopy analyzes the overtones of fundamental vibration that fall in the region from 4500 to 12000 $cm^{-1}$. NIR is sensitive to intermolecular forces, generally at C-H bands. Examples of such overtone bands include CH, $CH_2$ and $CH_3$.

Referring to FIG. 1, a probe 14 is inserted into the beaker 10 and liquid component 12(a). Probe 14 is in communication via a fiber optic cable 16 to a Near Infrared (NIR) spectrometer 20, also referred to as spectrometer 20. Spectrometer 20 can produce a spectrum indicative of the carbon-hydrogen bond in component 12(a). The spectrum can be plotted as absorbance (in absorbance units, AU) against wavenumber from 8000 to 4000 $cm^{-1}$.

Any one of a number of commercially available NIR spectrometers may be used. As an example, spectrometer 20 may be a Thermo-Scientific Nicolet™ 6700 Fourier Transform-IR (FT-IR) spectrometer (available from Thermo Fisher Scientific Inc., Waltham, Mass.). The spectrometer utilizes a light source and a DTGS detector, and 64 scans are averaged at a resolution of 4 $cm^{-1}$ with a 0.5 mm $CaF_2$ liquid transmission cell. The wavelength range used can be from 900 to 2500 nm. This particular spectrometer was used to generate the spectra in the examples herein. Other NIR spectrometers that may be used may be purchased from Agilent Technologies (Santa Clara Calif.) and Bruker Optics Inc. (Billerica, Mass.). The spectrometers are characterized by their ability to create NIR spectrum from the components of interest.

For each of the other components 12 of interest which are to be analyzed for their concentration in a commingled mixture, an NIR component spectrum for that particular component is generated in a manner as described above. Each spectrum is recorded on a memory in a computer 22. Computer 22 has commercially available chemometrics software loaded thereon to analyze a plurality of spectra.

Some NIR spectrometers have sample cells in which samples may be placed and a spectrum can be generated. In such cases, probes need not be used to generate a spectrum. However, for monitored samples in situ operations, preferably a probe is placed in situ in a conduit or piping containing the mixture of components 12 which are to be analyzed for their content.

Calibration Mixtures and Spectra

Table 1 lists discrete combinations of crude oil components 1, 2, and 3 in which the three components were mixed with a solvent, toluene, to produce mixtures 1-19. Crude oil components 1, 2 and 3 were produced from subterranean reservoirs from different regions of the world. In this instance, the mixtures 1-19 are expressed as weight percent of the crude oil components with the remaining weight percentage being toluene. For instance, in the first mixture there is 24.9 wt. % Component 1, 12.4 wt. % Component 2, and 12.3 wt. % Component 3 and the remaining 51.3 wt. % toluene.

TABLE 1

Measured and Calibrated Mixtures

| Mixture No. | Comp. 1 (wt. %) | Comp. 2 (wt. %) | Comp. 3 (wt. %) | Usage | Measured (Actual) | Calculated by NIR | Difference (Calculated-Actual) |
|---|---|---|---|---|---|---|---|
| 1 | 24.9 | 12.4 | 12.3 | Calibration | 12.4 | 12.3 | −0.1 |
| 2 | 12.5 | 24.9 | 12.5 | Calibration | 24.9 | 25.0 | 0.1 |
| 3 | 0.0 | 36.6 | 12.2 | Calibration | 36.6 | 36.4 | −0.2 |
| 4 | 12.4 | 0 | 36.7 | Calibration | 0.0 | 0.1 | 0.1 |
| 5 | 37.1 | 36.9 | 12.9 | Calibration | 36.9 | 36.9 | 0.0 |
| 6 | 12.3 | 36.9 | 0.0 | Calibration | 36.9 | 36.9 | 0 |
| 7 | 12.5 | 12.6 | 25.0 | Calibration | 12.6 | 12.5 | −0.1 |
| 8 | 37.5 | 12.5 | 0.0 | Calibration | 12.5 | 12.6 | 0.1 |
| 9 | 0.0 | 12.5 | 37.6 | Calibration | 12.5 | 12.7 | 0.2 |
| 10 | 16.7 | 17.0 | 16.6 | Calibration | 17.0 | 16.8 | −0.2 |
| 11 | 49.8 | 0 | 0 | Calibration | 0.0 | −0.1 | −0.1 |
| 12 | 24.8 | 24.9 | 0.0 | Calibration | 24.9 | 25.1 | 0.2 |
| 13 | 25.0 | 0.0 | 25.0 | Calibration | 0.0 | −0.1 | −0.1 |
| 14 | 0.0 | 24.7 | 24.7 | Calibration | 24.7 | 24.5 | −0.2 |
| 15 | 0.0 | 50.0 | 0 | Calibration | 50.0 | 50.1 | 0.1 |
| 16 | 0.0 | 0.0 | 49.4 | Calibration | 0.0 | 0.1 | 0.1 |
| 17 | 9.4 | 35.3 | 5.2 | Validation | 35.3 | 32.0 | −3.3 |
| 18 | 14.8 | 20.2 | 14.9 | Validation | 20.2 | 18.2 | −2.0 |
| 19 | 4.1 | 16.6 | 29.3 | Validation | 16.6 | 19.6 | 3.0 |

The 19 mixtures were carefully mixed to provide distinct combinations on known wt. % of base components. The last three columns compare the actual measured and calculated values of the weight percentage of Component 2.

Calibration Models Generated from Spectra

Figure 2:
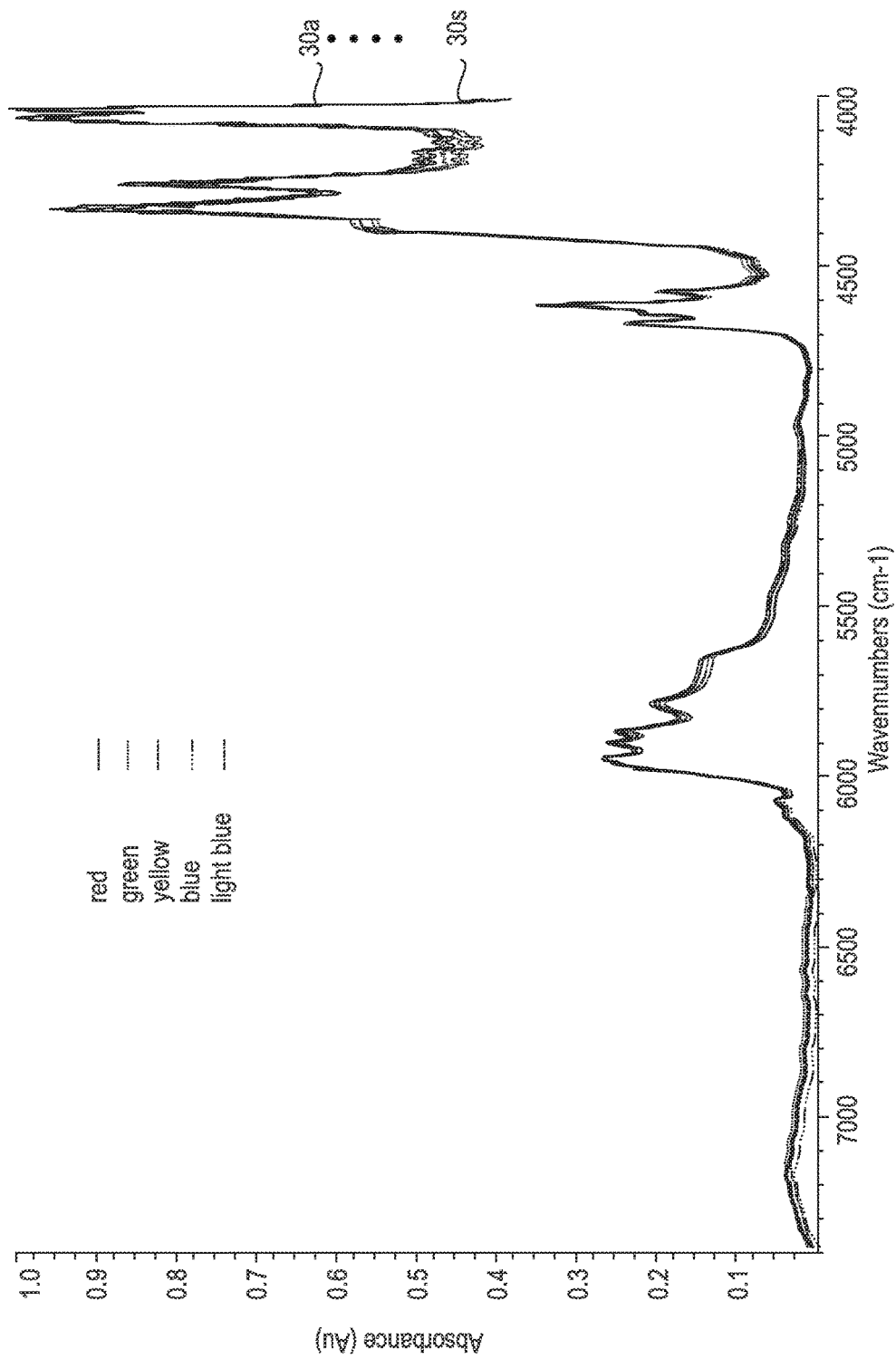
FIG. 2 is a plot of overlaid spectra from sixteen calibration mixtures and three monitored mixtures.
Figure 3A:
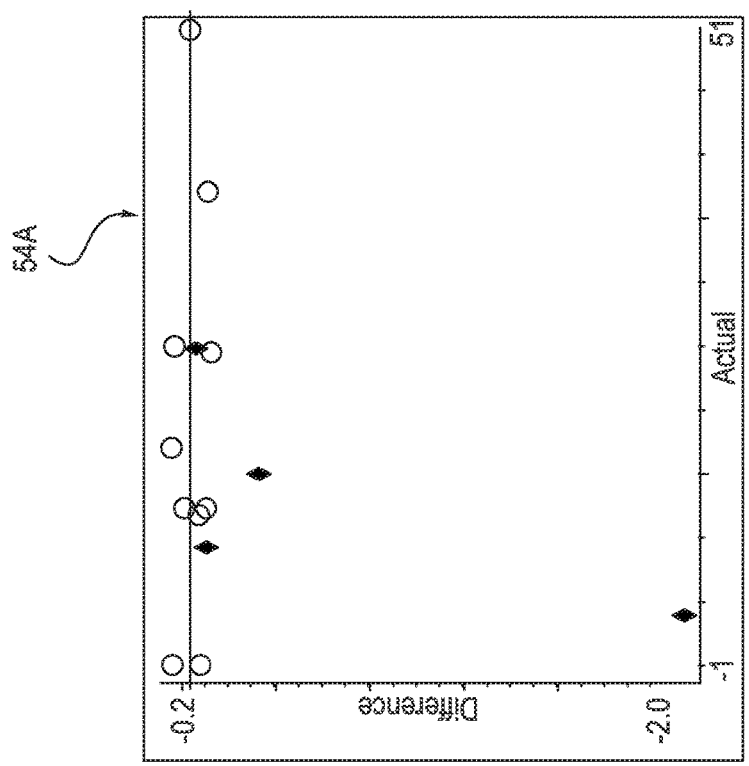
FIGS. 3A-C are graphs showing the close correlation between calibration mixtures of each known composition and estimates made by using NIR spectra in accordance with the present analytical method.
Figure 3B:
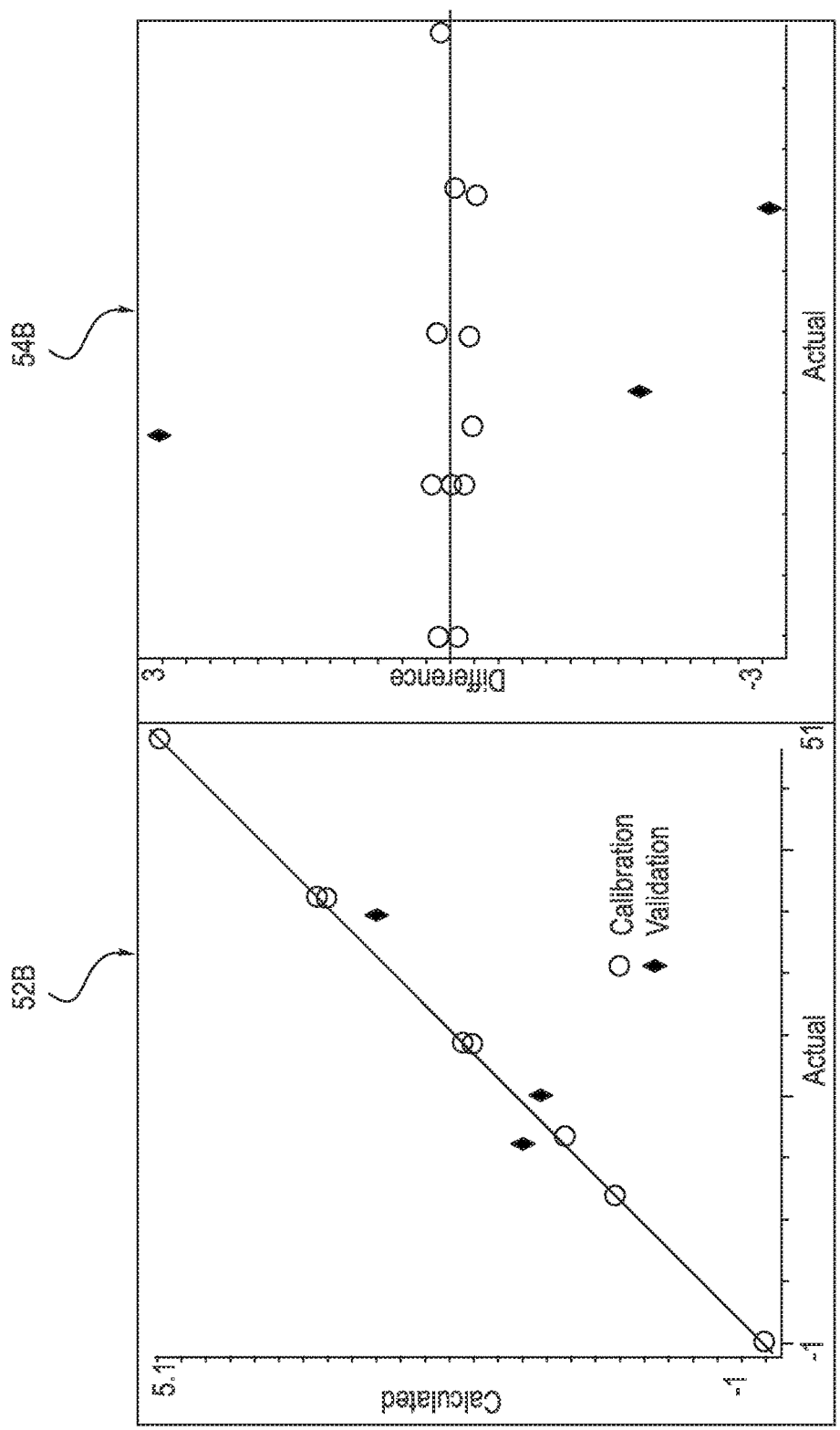
Figure 3C:
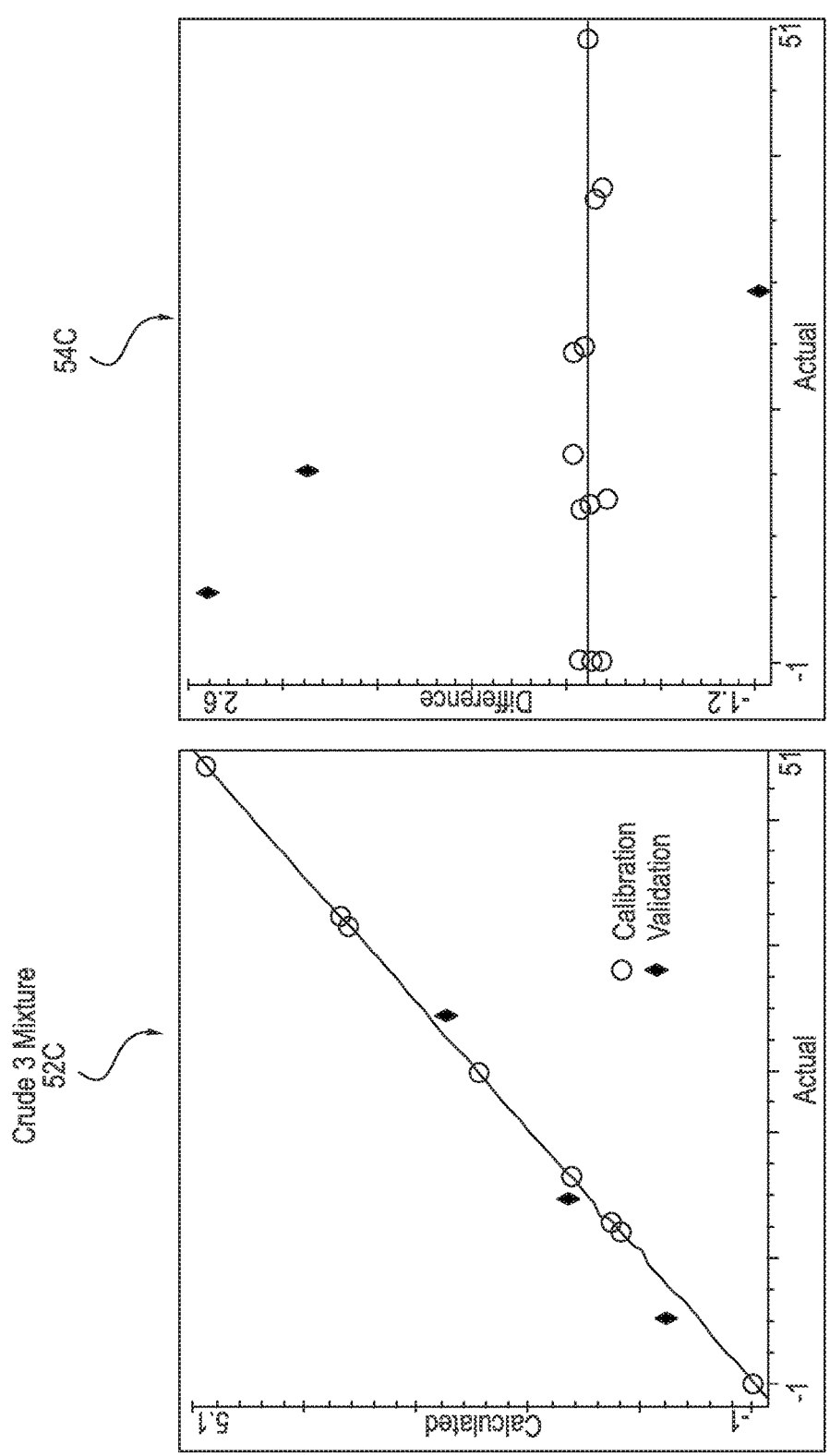

FIG. 2 displays overlaid IR spectra 30 of the nineteen spectra 30a-30s associated with mixtures 1-19. The spectra 30 were analyzed by Thermo Scientific™ TQ Analyst™ Professional Edition Software (available from Thermo Fisher Scientific Inc., Waltham, Mass.). Calibrated models 52A, 52B and 52C were generated for each of the crude oil components 1, 2, and 3, as shown in FIGS. 3A, 3B and 3C. Accompanying each of the calibration models 52A, 52B and 52C were error models 54A, 54B and 54C.

A commingled mixture of components, referred to as a monitored mixture, was then analyzed by a spectrometer 20 to generate a monitored spectrum. This is done in the same fashion as was described above with respect to the component spectra and mixture spectra. Computer 22 then used calibration models 52A, 52B and 52C to determine the wt % of crude oil components 1, 2, and 3 in the monitored mixture using the chemometric software. As seen in Table 1, the NIR calculated values for the monitored mixture are quite close to those of the actually measured mixtures. Note the usage on the last three mixtures (mixtures 17-19) are for the monitored mixtures or validation mixtures rather than calibration mixtures (mixtures 1-16).

Example 1

Figure 4:
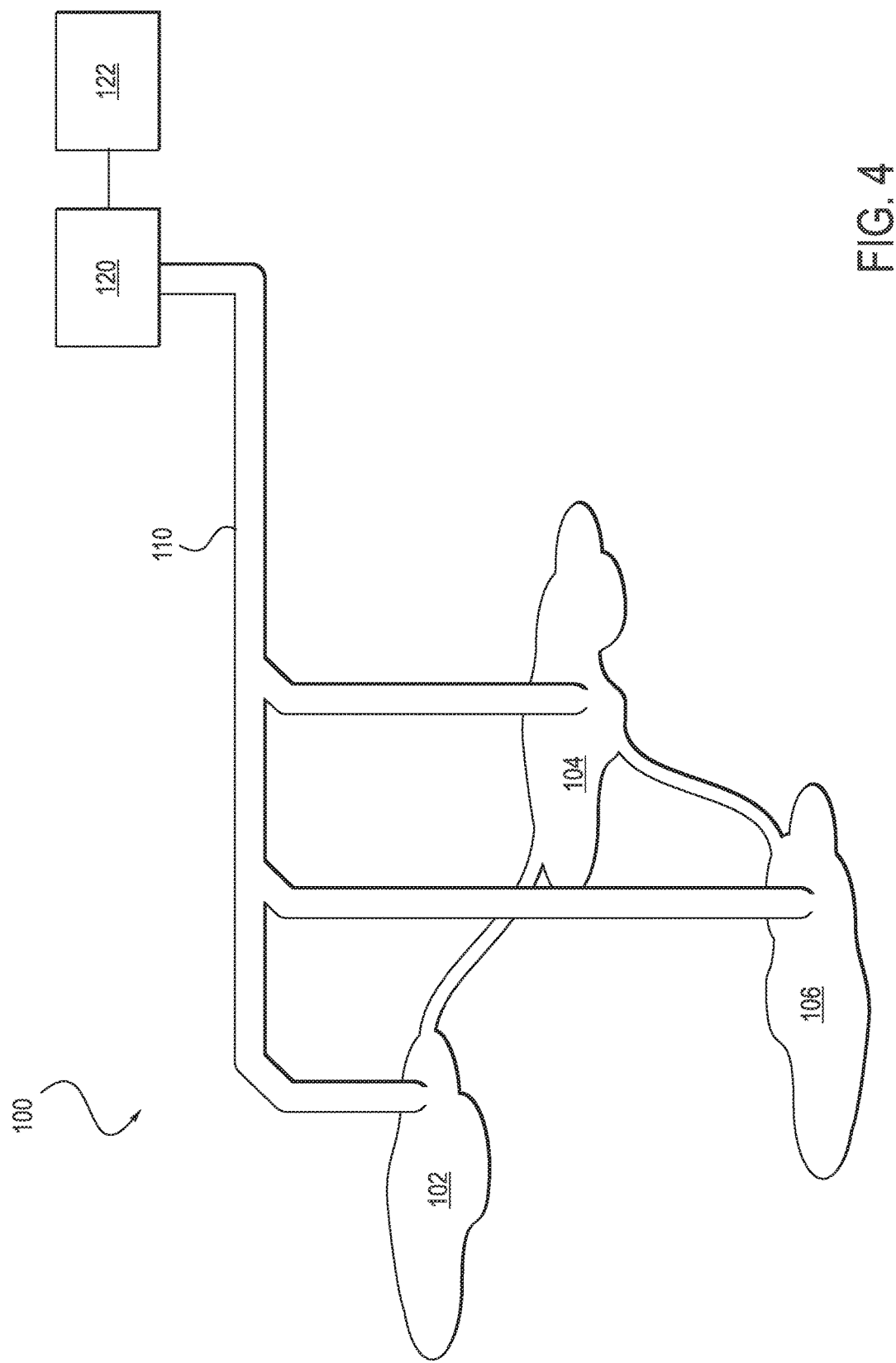
FIG. 4 is a schematic of a system including a plurality of subterranean reservoirs from which hydrocarbons are produced and then commingled to produce a mixture of hydrocarbon components with the mixture then being inspected by NIR to determine the relative amounts received from each of the reservoirs.

FIG. 4 illustrates a system 100 using the methodology described above. Base components, i.e., crude oil samples, are withdrawn from distinct reservoirs 102, 104 and 106. These component samples are probed and component spectra of these samples are generated. Next, three calibration mixtures, and more preferably greater than 15 calibration mixtures are made from the three base or reservoir components. Each of the mixtures has discrete concentrations of components over a range which is reflective of what potential mixtures might be produced in the commingled components. These calibration mixtures are examined with a spectrometer 120 and calibration spectra are generated. The component and calibration spectra are input into the chemometrics software of a computer 122 and calibration models, similar to those shown in FIGS. 3A-C are generated. Note that although illustrated as separate components, the spectrometer 120 and computer 122 may be combined into a single unit.

Common wellbore 110 receives fluids from each of reservoirs 102, 104 and 106 producing a commingled mixture of components to be monitored. A system, including a spectrometer 120 and computer 122, is used to monitor these commingled fluids from wellbore 110. A NIR spectrum from the commingled fluids of wellbore 110 is generated by spectrometer 120. Computer 122 is loaded with the calibration models and by comparing the spectra of the commingled fluids with the calibration models, the relative amounts of fluids received from reservoirs 102, 104 and 106 can be determined. As described above, the calibration models are used to determine the weight % of each of the components produced form reservoirs 102, 104 and 106.

Example 2

FIG. 5 illustrates another system 200 using the methodology described above. Components, i.e., samples, are withdrawn from storage tanks 202, 204 and 206. The components are analyzed and spectra of these individual samples are generated. Next, three calibration mixtures (not shown) are made from the components, each of the mixtures having discrete concentrations of components. These calibration mixtures are examined with NIR spectrometer and calibration spectra are generated. Calibration models are created from these spectra.

A common pipeline 210 receives fluids from each of storage tanks 202, 204 and 206. The commingled fluids are examined by NIR spectrometer 220 and the spectra of the commingled fluids are generated. As described above, the calibration models, stored in a computer memory of computer 222, are used to determine the weight % of each of the components produced from storage tanks 202, 204 and 206. The method may be adjusted to obtain the relative percentages of fluids from the tanks such as % volume or % weight.

Example 3

FIG. 6A illustrates a production system 300 wherein heavy oil is produced from a subterranean formation 302. Overburden 304 lies atop formation 302. A pump jack 301 or other source is used to withdraw the fluids from formation 302 via production tubing 306 to deliver to fluids to a wellhead 310. The subterranean formation receives diluting solvents, such as naphtha, to enhance the flowability of the heavy oil. Water is also generally present in subterranean formation 302.

In one embodiment, components to be analyzed include heavy oil and naphtha solvent. Each of these components is individually obtained and examined for their respective NIR spectrum. Calibration models are made by making mixtures of the heavy oil and naphtha over a wide range of combinations of these components.

FIG. 6B illustrates a fragmented view showing that system 300 includes production tubing 306 for receiving production fluids from the subterranean reservoir 302 and a reinjection conduit 308 located within production tubing 306 for reinjecting naphtha solvent into the subterranean formation, when needed, to enhance production.

Figure 7:
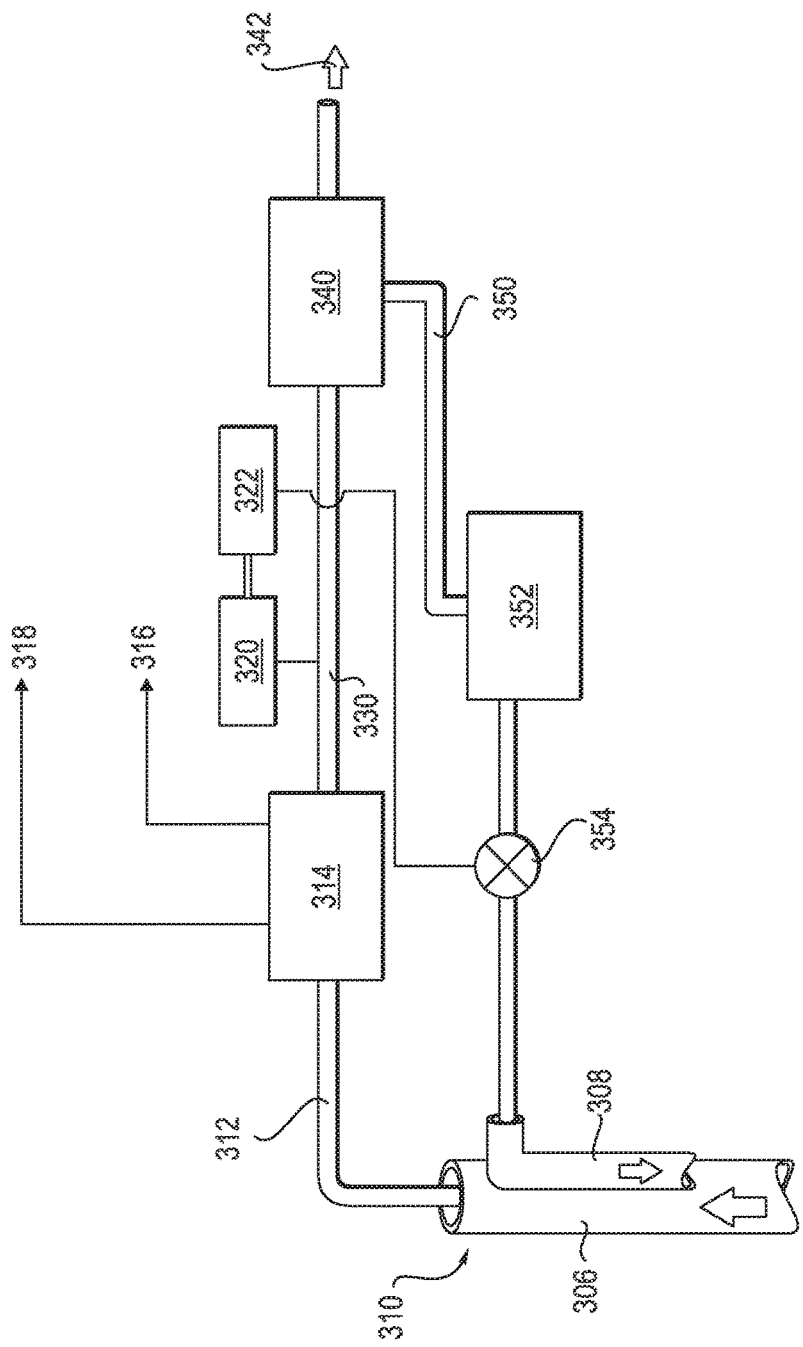
FIG. 7 is a schematic drawing of produced fluids from the wellbore of FIG. 6A being separated and the naphtha and heavy oil being monitored in situ by an NIR spectrometer with NIR spectrum being analyzed by a predetermined calibration model stored on a computer to determine the concentrations of the naphtha solvent in the naphtha and heavy oil mixture so that separated naphtha can be reinjected if the naphtha concentration in the mixture falls below a predetermined concentration.

FIG. 7 is a schematic drawing of surface facilities of production system 300 according to one embodiment. Wellhead 310 receives the production fluids 312 from the subterranean formation. A first separator 314 is used to remove gas 316 and water 318 from produced fluids 312, leaving a mixture 330 of naphtha solvent and heavy oil. The separated mixture 330 of naphtha and heavy oil is subjected to evaluation using spectrometer 320. In this instance, ideally spectrometer 320 uses a probe (not shown) in situ to examine or monitor the heavy oil and naphtha mixture 330 and to generate a corresponding NIR monitor spectra. Spectrometer 320 and computer 322, loaded with calibration models produced by the calibration mixture of heavy oil and naphtha, are used to calculate the concentration of naphtha and heavy oil in the mixture 330.

The heavy oil and naphtha are then separated using a separator 340. The separated heavy oil 342 is sent on to further processing facilities such as refinery. The separated naphtha solvent 350 is ideally recovered and stored in a storage tank 352. When the calculated concentration of the naphtha in the heavy oil and naphtha mixture 330 falls below a predetermined level, as determined by computer 322, naphtha from storage tank 352 may be reinjected by conduit 308 into subterranean formation 302 to again enhance the flowability of heavy oil from reservoir 302. Computer 322 may be used to activate a valve 354 to allow naphtha to flow back into injection conduit 308 until the level of naphtha solvent is again a desired level. At such time valve 354 can be closed.

While in the foregoing specification this invention has been described in relation to certain preferred embodiments thereof, and many details have been set forth for purpose of illustration, it will be apparent to those skilled in the art that the invention is susceptible to alteration and that certain other details described herein can vary considerably without departing from the basic principles of the invention.

What is claimed is:

1. A method of estimating the relative concentration of components contained in an unknown mixture of the components, each component being a mixture of different hydrocarbon molecular species, the method comprising the steps of:
   (a) receiving at least two components from discrete sources;
   (b) producing at least two calibration mixtures comprising the at least two components from discrete sources and a liquid hydrocarbon diluting solvent selected from the group consisting of naphtha, alkane solvents, refined hydrocarbon solvents, and mixtures thereof, each of the at least two calibration mixtures having different concentrations of the at least two components;
   (c) acquiring NIR calibration spectra for each of the calibration mixtures;
   (d) acquiring NIR spectra for each of the components received from discrete sources;
   (e) inputting the respective concentration and calibration spectra for each of the calibration mixtures, and the NIR spectra for each of the components received from discrete sources, into a chemometrics software program and generating a calibration model;
   (f) acquiring NIR spectra for the unknown mixture of the components from the discrete sources and providing the NIR spectra to the calibration model of (e); and
   (g) calculating the relative concentration of each of the components from the discrete sources utilizing the calibration model of step (e).

2. The method of claim 1 wherein:
the calibration mixture and the unknown mixture contain at least three components, including the first component, the second component, and a third hydrocarbon component.

3. The method of claim 1 wherein:
the calibration mixture and the unknown mixture contain at least four components, including the first component, the second component, a third hydrocarbon component, and a fourth hydrocarbon component.

4. The method of claim 1 wherein:
the calibration mixture is made of a liquid hydrocarbon and a liquid hydrocarbon solvent.

5. The method of claim 2 wherein:
the calibration mixture is made of at least two liquid hydrocarbons and at least one liquid hydrocarbon solvent.

6. The method of claim 1 wherein:
the discrete sources of components are individual storage tanks of components.

7. The method of claim 1 wherein:
the storage tanks contain hydrocarbons of differing compositions.

8. The method of claim 1 wherein:
the discrete sources comprise one or more subterranean reservoirs containing hydrocarbons of differing compositions.

9. The method of claim 1 wherein:
the components are received from at least one wellbore in fluid communication with one or more subterranean reservoirs containing heavy oil.

10. The method of claim 9 wherein:
the first component comprises heavy oil and the second component comprises a liquid hydrocarbon solvent.

11. The method of claim 10 wherein:
the concentration of the solvent is monitored; and
solvent is added to the subterranean formation if the concentration of the solvent in the monitored mixture falls below a predetermined concentration.

12. The method of claim 11 wherein:
the mixture from the wellbore is measured downstream of the wellbore.

13. The method of claim 5 wherein:
the calibration mixture comprises heavy oil and a liquid hydrocarbon solvent; and separated solvent is reinjected into the subterranean formation.

14. The method of claim 1 wherein:

the calibrated mixtures are mixed in a laboratory and the mixture calibration is calculated by the chemometrics software in the laboratory;

the mixture calibration is imported into a computer at the site of a hydrocarbon producing well; and the spectrum is acquired in situ at the well for well fluids from the well by a spectrometer and the concentration of the components of the unknown mixture is calculated using the calibration model.

\* \* \* \* \*